(12) United States Patent
Ekhoff

(10) Patent No.: US 6,781,684 B1
(45) Date of Patent: Aug. 24, 2004

(54) WORKPIECE LEVITATION USING ALTERNATING POSITIVE AND NEGATIVE PRESSURE FLOWS

(76) Inventor: Donald L. Ekhoff, 15105 Concord Cir., Morgan Hill, CA (US) 95037

( * ) Notice: Subject to any disclaimer, the term of this patent is extended or adjusted under 35 U.S.C. 154(b) by 637 days.

(21) Appl. No.: 09/708,768

(22) Filed: Nov. 7, 2000

(51) Int. Cl.[7] .......................... G01N 21/00; G01B 11/30
(52) U.S. Cl. ................................ 356/237.1; 356/239.7; 356/239.8; 356/600
(58) Field of Search .......................... 356/237.1–237.6, 356/239.1–239.8, 600, 601

(56) References Cited

U.S. PATENT DOCUMENTS

| | | | |
|---|---|---|---|
| 5,459,576 A | 10/1995 | Brunfeld et al. | 356/353 |
| 5,575,746 A | 11/1996 | Weder et al. | 493/154 |
| 5,724,140 A | 3/1998 | Haywood | 356/371 |
| 5,726,749 A | 3/1998 | Schave | 356/239 |
| 5,907,396 A | 5/1999 | Komatsu et al. | 356/237.1 |
| 6,359,686 B1 * | 3/2002 | Ariglio et al. | 356/239.1 |

* cited by examiner

Primary Examiner—Frank G. Font
Assistant Examiner—Amanda Merlino
(74) Attorney, Agent, or Firm—Law Offices of Terry McHugh

(57) ABSTRACT

A support structure utilizes a combination of positive pressure openings and negative pressure openings to precisely position a workpiece, such as a sheet of float glass. The positive pressure openings are supply openings that direct a flow of fluid, such as air, onto the surface of the workpiece. The negative pressure openings are exhaust openings that are used to regulate the leakage of fluid from between the workpiece and the support structure. In the preferred embodiment, the surface of the support structure includes raised regions that surround the exhaust openings and that function as self-regulating pinch valves. This arrangement enables an equilibrium condition to be quickly established and maintained upon placement of the workpiece on the support structure.

20 Claims, 7 Drawing Sheets

WORKPIECE LEVITATION USING ALTERNATING POSITIVE AND NEGATIVE PRESSURE FLOWS

TECHNICAL FIELD

The invention relates generally to systems and methods for supporting a workpiece in a position for inspection or other processing, and relates more particularly to levitating the workpiece with a defined pattern of levitation forces along the surface area of the workpiece.

BACKGROUND ART

There are a wide variety of manufacturing applications in which the detection of surface defects and irregularities plays an important role in determining manufacturing yield. As examples, semiconductor substrates on which integrated circuits are fabricated and masks that are used during the fabrication process should be free of particles, such as dust. As another example, glass used in the fabrication of flat panel displays and similar applications should not include surface defects such as bumps, pits and scratches.

Surface defects and irregularities can be optically detected. As one example, U.S. Pat. No. 5,459,576 to Brunfeld et al. describes an optical inspection system that includes a spatially coherent light source to illuminate the surface of a workpiece to be inspected. A single beam of laser light is modified to produce what is referred to as a "black beam." A "black beam" is defined as a beam that has an intensity of zero in the vicinity of the optical axis. The result is that when the undisturbed beam is detected by a detector close to the optical axis, the detector output is zero. However, if the beam encounters a defect, the balance is upset and the detector will register a non-zero output. This non-zero output provides quantitative information regarding the defect or irregularity.

An optical system for inspecting glass workpieces is described in U.S. Pat. No. 5,726,749 to Schave. A number of laser light sources are positioned on one side of the sheet of glass or other transparent material. A corresponding number of photosensitive position detectors are located on the opposite side. Light beams are directed from the laser sources through the transparent sheets to the position detectors. The angular deviation of each light beam which occurs as the light beam passes through the sheet affects the signal at the corresponding position detector. The signals generated as a result of angular deviation of the light beams from their optical axes are processed to provide information regarding the angular deviation values of the transparent sheet. The distortion is determined by the rate of change of the angular deviation and is calculated for comparison to preset standards, so as to determine if the transparent sheet is within acceptable quality control measures. The inspection system of Schave includes a conveyor for transporting the transparent sheets relative to the laser sources. The transparent sheets are supported on motor-driven belts.

While the use of motor-driven conveyor belts for optical inspection systems may provide acceptable results in some applications, other applications require a level of measurement preciseness that may not be achievable using standard mechanical approaches. An alternative approach is to use air pressure to levitate the workpiece to be inspected. A flat panel display may be more precisely inspected while being levitated by an air film.

A conventional air table for supporting a workpiece on an air film includes a work surface having an array of through holes. Pressurized air escapes from the through holes to apply a force to the workpiece. In some applications, the flatness of the workpiece may be affected by differences in the localized pressures applied to the workpiece. Laser scanning will detect very small changes in angular distortion of a flat panel display or other product that is susceptible to some bending as a result of non-uniformity in applied localized pressures.

A concern is that equalization of the air flow through the holes of the air table may not result in uniformity of localized pressures. For a conventional air table, the pressurized air escapes from the array of through holes to strike the workpiece and then leaks from the edges of the workpiece, unless the workpiece allows the passage of air. For a solid workpiece, the result is that the pressure is greatest at the central region of the workpiece and least at the edges, where the air is allowed to escape than at its edges. This may cause a "bulge" in the center region of the workpiece. This bulge will be detected as a surface irregularity during a laser scanning operation. Moreover, as consequences of the limited depth of field of detection optics, tangential error may cause the laser beam to miss the detector and DC error may occur.

What is needed is a system and method for levitating a workpiece in a manner that reduces susceptibility to angular distortions as a result of variations in localized pressures and overall pressure gradients.

SUMMARY OF THE INVENTION

Workpiece planarity is promoted by utilizing a support structure having reverse flow exhaust openings interspersed with supply openings that direct a levitating flow of fluid to impinge the workpiece. Rather than focusing on regulating the flow of supplied fluid to the fluid film region between the support structure and the workpiece, the focus is on regulating the air leakage path from the fluid film region. Specifically, lateral fluid flow to the edges of the workpiece is retarded. In the preferred embodiment, the work surface of the support structure includes planar raised regions about the exhaust openings, so that fluid flow is regulated on the basis of closure distance, in the same manner as a pinch valve. Also in the preferred embodiment, the fluid is a gas, such as air.

The air distribution supply holes are clustered around exhaust holes to provide localized cells of air flow at equilibrium conditions. Overall sizing and the associated pressure differentials through the holes are determined as a function of the overall system design and as a function of the need for all pressure cells to be operating with similar performance across the entire surface of the workpiece being supported. Additionally, it is often the case that there are flow cells that are uncovered as the workpiece is transported over the work surface. The supply holes and exhaust holes are therefore open to atmosphere and must be small enough so as to not degrade the performance of the cells still actively supporting the workpiece. Larger holes require a larger flow source and larger manifolds for distribution. Higher "flying heights" are a result of this increased flow.

In the operation of the method, gas is continuously fed through the supply openings. When the workpiece is positioned adjacent to the work surface of the support structure, the supplied gas pressure supports the workpiece. The combination of atmospheric pressure on the workpiece and reverse flow through the exhaust openings quickly causes the workpiece to drop close to the support structure. As a result, the workpiece approaches a position in which it blocks the exhaust openings, particularly in the embodiment in which the exhaust openings are within raised regions along the surface of the support structure. An equilibrium condition is soon established in which the gas supply volume equals the gas leakage volume. After the equilibrium condition has been reached, any external forces which tend to press the workpiece will cause an increase in the applied pressure. Conversely, any external forces which tend to separate the workpiece from the support structure will cause a pressure drop. The result is a self-managed "flying height." Depending upon the workpiece, the approach may operate to flatten curled or distorted material. For example, the workpiece may be a continuous web of flexible material.

Preferably, the support structure is non-particulating. The support structure may be a substantially planar "table" formed of a high density polypropylene, but other materials (e.g., aluminum) may be used. The work surface of the table may be white if the system is to be used in a clean room or may be black in order to facilitate inspection using the "black beam" technology. The support structure may include a manifold arrangement in which the supply openings are connected to a source of pressurized gas, while the exhaust openings are connected to a vacuum source. Optionally, a single pump may be used to provide both the gas pressurization for the supply openings and the partial vacuum condition for the exhaust openings. The capacity of the exhaust should exceed the flow of gas from the supply, so that lateral flow to the edges of the workpiece is retarded.

In operation, the supply arrangement provides the lift, while the exhaust arrangement regulates the height of the supported workpiece. Pressure from the supply openings will properly support a load if there is sufficient resistance to lateral flow to develop pockets of lifting pressure. The raised regions about the exhaust openings regulate the height by functioning as pinch valves. That is, the distances between the workpiece and planar upper surfaces of the raised regions will regulate the characteristics of the pockets, since these distances determine the flow rate into the exhaust openings.

The size of the support structure will depend upon the application. Contemplated applications include inspecting glass for flat panel displays, semiconductor wafers for the integrated circuit chip industry, and webs of flexible material. For the glass substrate application, the thickness of the glass may be in the range of 0.3 mm to 10 mm, but this is not critical. A flying height may be in the range of 0.05 to 0.5 mm.

While not critical, the supply openings may have a cross sectional area that is smaller than the cross sectional area of the exhaust openings. For example, the supply openings may have a diameter of 0.16 mm, while the exhaust openings may have a diameter of 0.8 mm. However, the supply openings preferably outnumber the exhaust openings.

DETAILED DESCRIPTION

Figure 1:
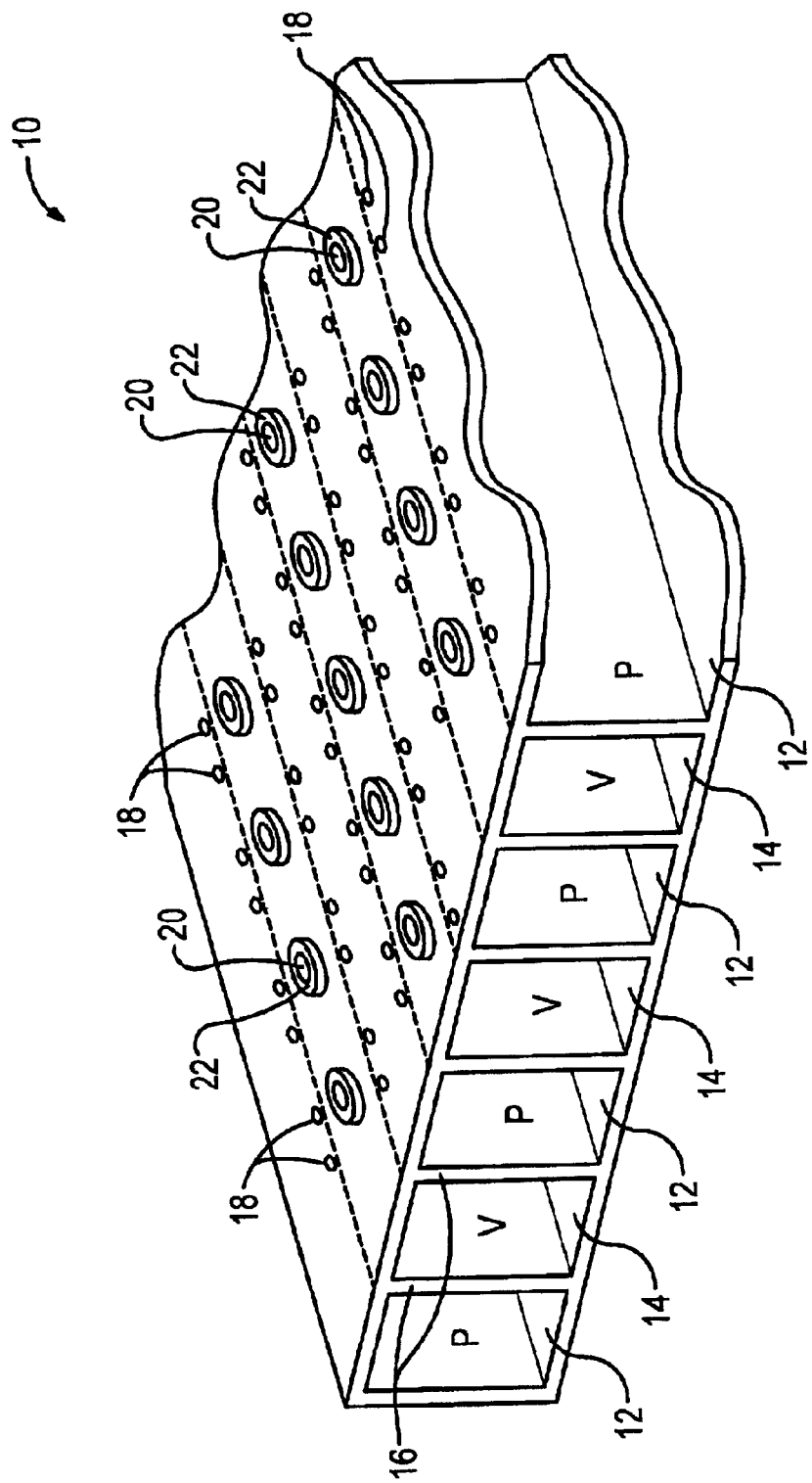
FIG. 1 is a perspective partial view of a support structure having exhaust openings and supply openings in accordance with one embodiment of the invention.
Figure 2:
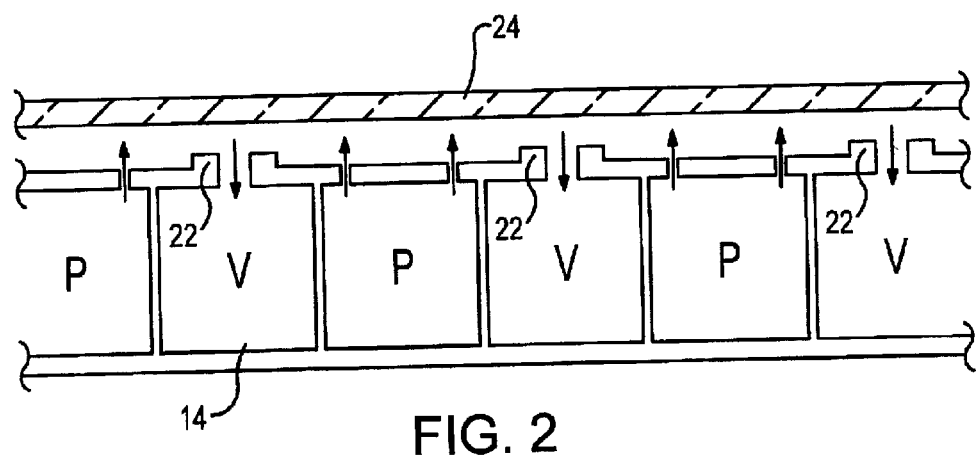
FIG. 2 is a partial side view of the support structure of FIG. 1, supporting a workpiece.
Figure 3:
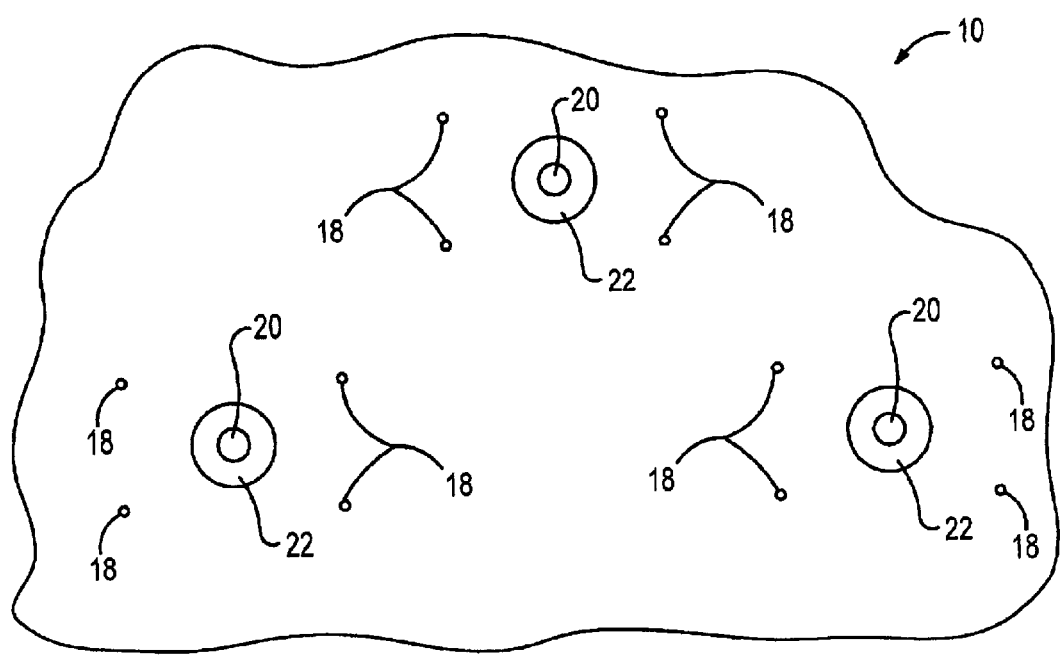
FIG. 3 is a partial top view of the support structure of FIG. 1.

With reference to FIGS. 1, 2 and 3, a support structure 10 for "floating" a workpiece is shown as including pressurized chambers (P) 12 and partial vacuum chambers (V) 14. The pressurized chambers 12 receive a continuous flow of pressurized fluid from a fluid source, not shown. The fluid is preferably gas and most preferably air. Adjacent chambers are separated by ribs 16.

Each pressurized chamber 12 is connected to a number of supply openings 18 within the upper wall of the support structure 10. Similarly, each vacuum chamber 14 is connected to a number of exhaust openings 20. In the preferred embodiment, the exhaust openings are surrounded by raised regions 22. While the support structure is shown as a one-piece member in FIG. 2, the raised regions 22 may be fabricated as separate elements. For example, a patterned layer may be formed on the work surface of the support structure to provide the raised regions. As another alternative, rings may be individually secured in position around the exhaust openings 20.

In the embodiment of FIGS. 1–3, each exhaust opening 20 is associated with four supply openings 18. However, this is not critical to the invention. The preferred arrangement of supply openings to exhaust openings will depend upon the application.

As indicated by the arrows in FIG. 2, the supply openings 18 direct a levitating flow of gas to impinge a workpiece 24. The force of the escaping gas lifts the workpiece from the raised regions 22 surrounding the exhaust openings 20. As a result, the gas is able to enter the vacuum chambers 14. There are a number of design goals in the fabrication of the support structure. Lateral flow of the gas to the edges of the workpiece 24 should be minimized. Only by providing sufficient resistance to lateral flow will self-regulating levitating pockets develop between the support structure and the workpiece. Thus, the exhaust capacity through the exhaust openings should exceed the supply of continuous flow through the supply openings.

The raised regions 22 surrounding the exhaust openings 20 should have a planar upper surface, so that the workpiece 24 rests on the planar upper surfaces and restricts flow through the exhaust openings 20 when the pressure from the supply openings 18 is insufficient to levitate the workpiece. Thus, the arrangement of raised regions 22 around the exhaust openings 20 provides a "pinch valve" capability. That is, servo valving regulates the "flying height" of the workpiece above the surface of the support structure 10.

In operation, when the workpiece 24 is positioned on the support structure 10, the workpiece will initially rest on the planar surfaces of the raised regions 22. The combination of atmospheric pressure on the workpiece and vacuum pressure via the exhaust openings 20 counteracts the force provided by the continuous flow of gas through the supply openings 18. However, the force of gas impinging upon the workpiece is sufficient to lift the workpiece from the raised regions 22. An equilibrium condition is soon established in which the gas supply volume equals the gas leakage volume. Upon reaching this equilibrium condition, any external forces which tend to press the workpiece closer to the support structure will cause a higher pressure condition, while any external forces which tend to separate the workpiece from the support structure will cause a pressure drop. The result is a self-managed "flying height."

Depending upon the workpiece, the localized pressures provided by the support structure 10 will tend to flatten curled or distorted material. For example, if a workpiece 24 has a downwardly curled edge, the localized pressure at the central region of the workpiece will stabilize, but will be different than the localized pressure at the curled edge. The downward curl places the edge of the workpiece closer to the surface of the support structure than the central region of the workpiece. Therefore, there will be a higher pressure at the edge. This higher pressure tends to flatten the workpiece, if the workpiece is sufficiently flexible. In one application, the workpiece is a continuous web of flexible material.

Preferably, the support structure 10 is formed of a non-particulating material. The support structure may be a substantially planar "table" formed of a high density polypropylene, but other materials may be used (e.g., aluminum). The work surface of the table may be white, if the system is to be used in a cleanroom, or may be black in order to facilitate inspection using "black beam" technology. The support structure may include a manifold arrangement in which the supply openings 18 are connected to a source of pressurized gas, while the exhaust openings 20 are connected to a vacuum source. Optionally, a single pump may be used to provide both the gas pressurization of the supply openings and a partial vacuum condition for the exhaust openings. As previously noted, the capacity of the exhaust should exceed the flow of gas from the supply, so that lateral flow to the edges of the workpiece 24 is retarded.

Exemplary dimensions will be described for an application in which the workpiece 24 is float glass for a flat panel display. However, as previously noted, the dimensions and the associated pressure differentials through the holes are determined as a function of the overall system design and as a function of the need for all pressure cells to be operating with similar performance across the entire surface of the workpiece being supported. An acceptable thickness of the ribs 16 and the walls of the support structure 10 is 0.8 mm. The height of the support structure as viewed in FIG. 2 may be 10 mm, and the pitch of the chambers 12 and 14 may be 10.4 mm. The height of the raised regions 22 above the work surface of the support structure may be 0.0762 mm. Practical considerations may limit a monolithic support structure to be under 1220 mm by 2440 mm, but monolithic support structures may be connected together to form larger structures, or alternative approaches to forming monolithic support structures may be developed.

The thickness of the float glass may be in the range of 0.3 mm to 1.1 mm. The flying height of the glass above the support structure 10 should be in the range of 0.05 mm to 0.5 mm, with a positioning tolerance of ±20 $\mu$m. "Plumbing" issues may cause variations beyond this tolerance over the entire area of the workpiece, but the variation can be tightly and repeatedly controlled within the region of optical inspection scan.

Glass angular deviation (or "wobble") is largely a function of the pitch of the chambers 12 and 14 and the stiffness of the supporting gas film. This is one of the primary reasons for having a relatively small chamber pitch.

In one embodiment, the supply openings 18 are covered and uncovered in a synchronous manner to reduce any lifting or drooping of the workpiece edges. While the support structure has been described with reference to supporting glass, other materials may be levitated above the support structure. For example, the support structure may be used to precisely position a semiconductor wafer or even a continuous web of flexible material.

Figure 4:
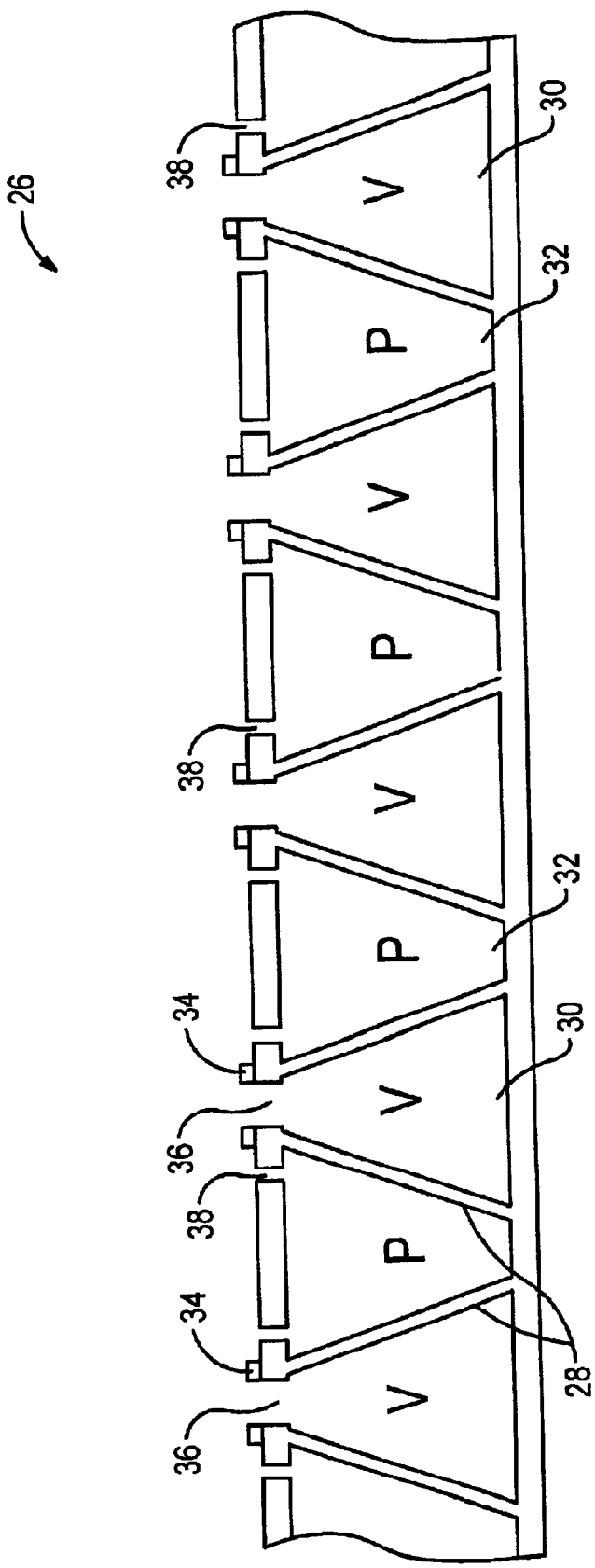
FIG. 4 is a partial side view of a second embodiment of the invention.

FIG. 4 shows an alternative embodiment of a support structure 26 in accordance with the invention. One difference between the support structure of FIG. 4 and the support structure of FIG. 1 is that the ribs 28 which separate vacuum chambers 30 from pressurized chambers 32 are diagonal members, rather than vertical members. Another difference is that annular members 34 are formed on a work surface of the support structure to provide the raised regions that surround the exhaust openings 36. This is in comparison to the monolithic support member 10 of FIG. 1. While the operation of the support structure 26 is substantially identical to the one described with reference to FIGS. 1–3, there may be fabrication advantages to the diagonal ribs 28 and/or the separate annular members 34.

Each vacuum chamber 30 is connected to a number of exhaust openings 36, while each pressurized chamber 32 is connected to a number of supply openings 38. The arrangement of exhaust openings to supply openings may be similar to the one shown in FIG. 1, but this is not critical. The pressure within the pressurized chambers 32 may be one pound per square inch (psi), but a pressure as low as 0.05 psi has been tested with acceptable results. It is not only the mass of the workpiece that forces the workpiece toward the work surface of the support structure 26. Atmospheric pressure also will force the product downwardly, if the vacuum chambers 30 are held at partial vacuum. Thus, while the described approach will work if the vacuum chambers are held at ambient, the degree of control will be reduced.

Figure 5:
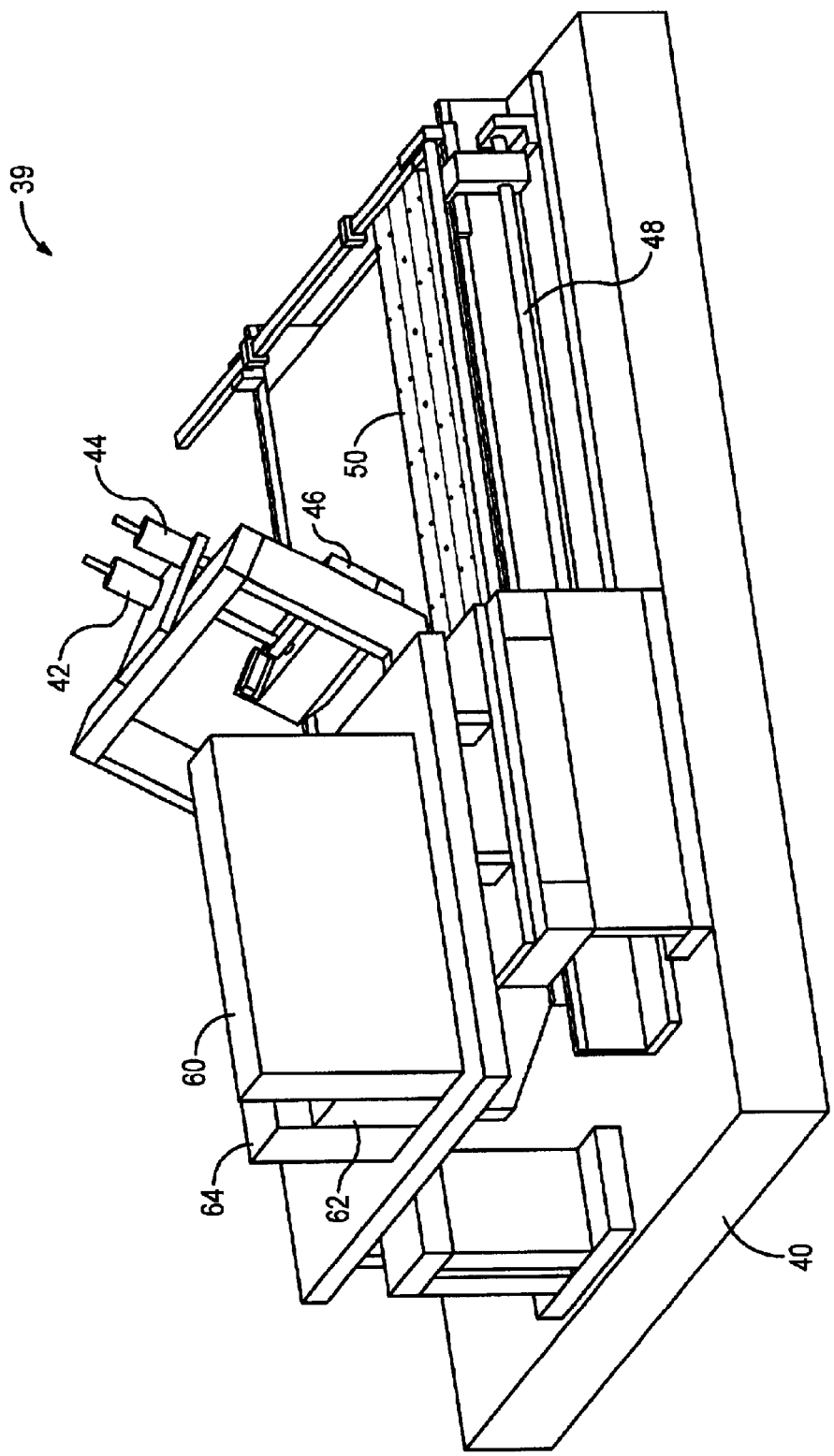
FIG. 5 is a perspective view of an acceptable optical inspection system that utilizes the support structure of FIGS. 1–3.

As previously noted, the levitation approach may be used in an optical inspection system. FIG. 5 illustrates an exemplary system. The components of the inspection system 39 are mounted on a table 40. The components include a pair of laser sources 42 and 44. However, the use of two laser sources is not critical. The optical arrangement also includes one or more detectors 46, as well as focusing elements. A rail system 48 allows movement of the optical arrangement relative to a pneumatic support structure 50 of the type described above. Thus, the laser sources 42 and 44 move longitudinally while the beams from the laser sources are scanned in a width-wise direction. Alternatively, the support structure 50 may move relative to a fixed optical arrangement.

Figure 6:
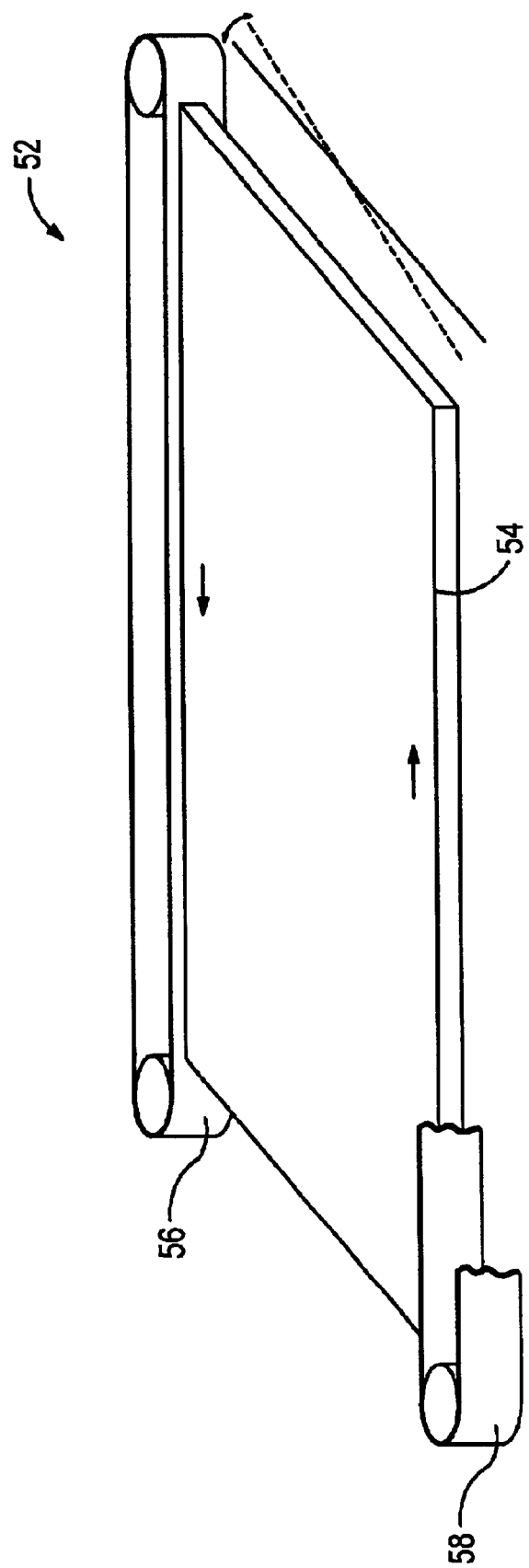
FIG. 6 is a perspective view of a mechanism for supporting the workpiece.

FIG. 6 illustrates a transport mechanism 52 for a glass workpiece 54 of the type used in the flat panel display industry. Continuous belts 56 and 58 provide edge contact with the glass, because the support structure has a tilt bias toward it. In order to translate the workpiece so as to allow scanning of the entire workpiece, it is only necessary to tilt it in the other direction in order to allow it to fall to the other side.

Returning to FIG. 5, the example of the inspection system 39 is shown as having three upright members 60, 62 and 64. These members are simplified representations of components such as the pump or pumps for providing the pressurization and vacuum conditions for operation of the support structure 50, the computer capability for processing the data, and the display device for visually presenting or for printing the results.

Figure 7:
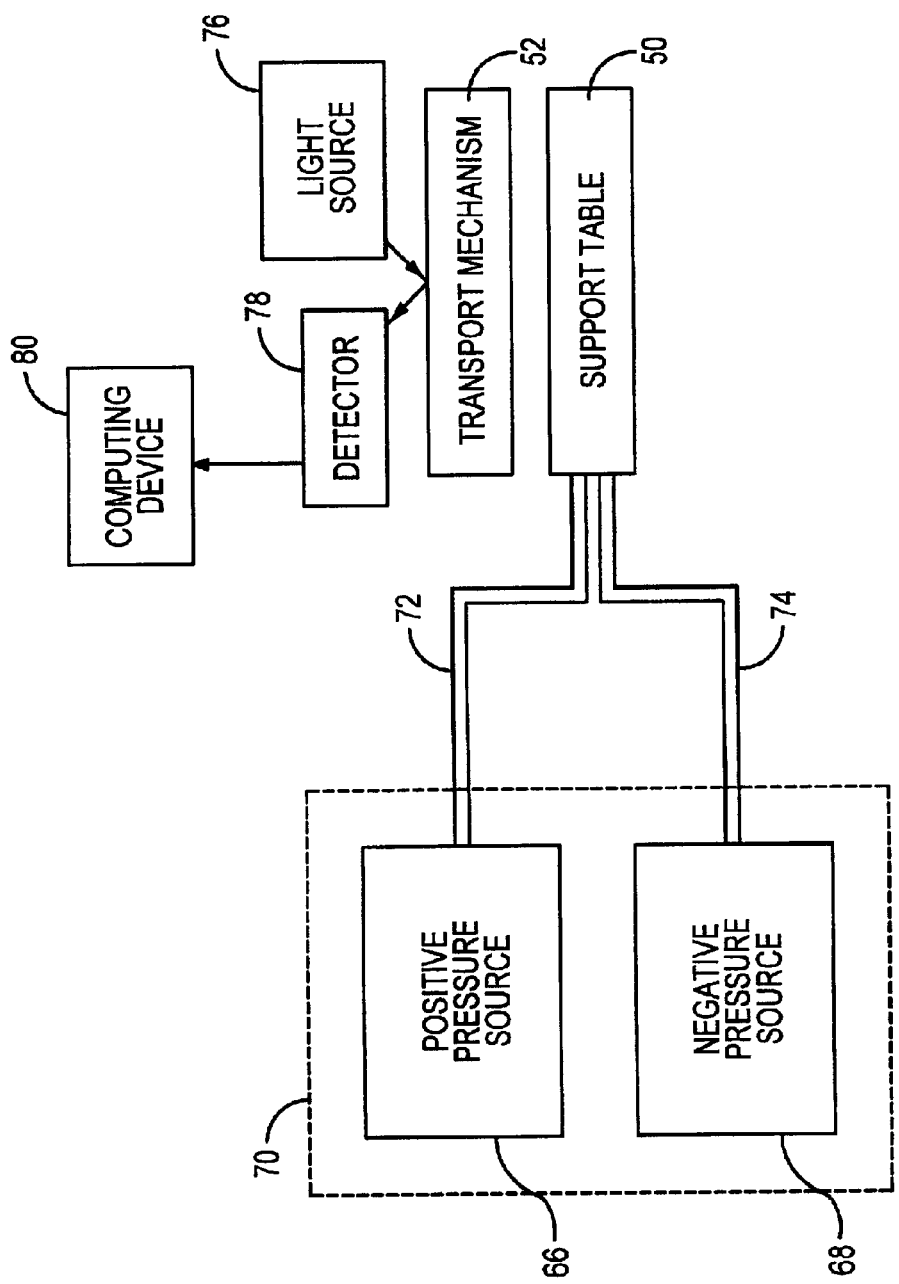
FIG. 7 is a schematic view of components for the inspection system of FIG. 5.

The components are also shown schematically in FIG. 7. The support structure 50 is shown as being a table that is connected to separate positive and negative pressure sources 66 and 68, respectively. However, a single pump may be used to provide both the positive pressure within the pressure chambers of the support structure and the negative pressure within the vacuum chambers of the support structure. The ability to use a single pump is represented by the dashed lines 70. Fluid conduits 72 and 74 couple the sources to the support structure.

The transport mechanism 52 may be used to manipulate the workpiece, as described above with reference to FIG. 6. One or more light sources 76 direct a beam onto the workpiece that is levitated above the support structure 50. In the embodiment of FIG. 7, the light beam is reflected from the workpiece and is used to obtain quantitative information by operation of a detector 78 and a computing device 80, such as a personal computer. Black beam technology may be used in the optical system of FIG. 7. The support structure 50 provides a self-managed flying height for the workpiece that is inspected, thereby providing a precise and repeatable means for properly positioning the workpiece relative to the light source 76 and the detector 78.

Figure 8:
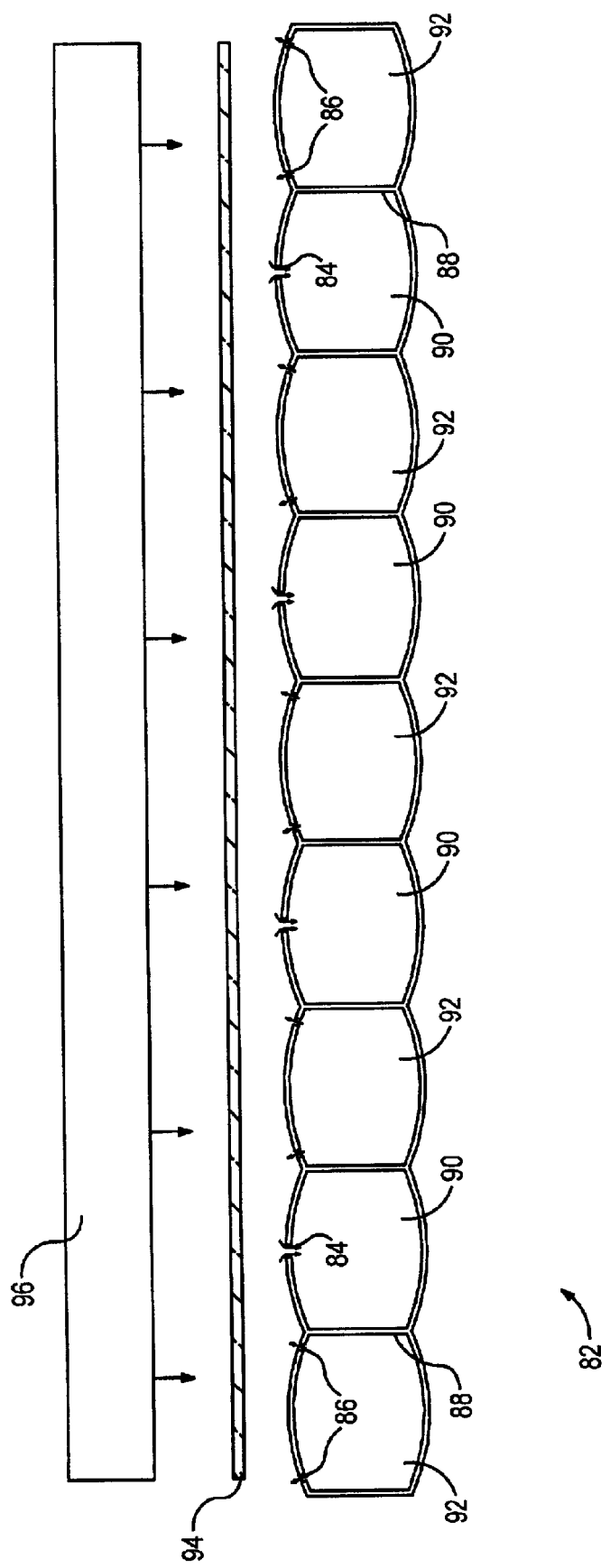
FIG. 8 is a third embodiment of a support structure for levitating a workpiece in accordance with the invention.

FIG. 8 shows another embodiment of the invention. In this embodiment, the surface of the support structure 82 forms the raised regions for exhaust openings 84. That is, the exhaust openings 84 are positioned at crests along the work surface of the support structure 82. Supply openings 86 are located at troughs along the work surface. Vertical ribs 88 separate vacuum chambers 90 from pressurized chambers 92.

In operation, a workpiece 94 is supported in the same manner as described with reference to FIGS. 1–4. The workpiece is levitated at a regulated "flying height" by the cooperation of the pressurized gas flow from the supply openings 86 and the reverse flow into the exhaust openings 84. Optionally, the system may include a means for providing active control over the flying height of the workpiece 94. That is, a mechanism for applying clamping force to the rear side of the workpiece may be employed. In FIG. 8, a source 96 of pneumatic pressure is used for this purpose. This active pneumatic control is particularly useful for applications in which the curvature of the workpiece is relatively easily influenced. A glass workpiece can be flattened by applying a pneumatic pressure that approaches one-third atmosphere, but only to a limited degree. The applied pneumatic pressure is balanced against the gas support film between the workpiece 94 and the support structure 82. The stiffness characteristics of the gas support film define the ability to flatten the glass.

What is claimed is:

1. A system for levitating workpieces comprising:
   a support structure that includes a work surface having a plurality of supply openings distributed among a plurality of exhaust openings, said work surface having raised regions at said exhaust openings; and
   source means in communication with said supply openings for supplying a continuous flow of fluid through said supply openings at a pressure selected to levitate a workpiece that is adjacent to said work surface, said exhaust openings being maintained at a pressure that enables a reverse flow of said fluid into said exhaust openings.

2. The system of claim 1 wherein said raised regions surround said exhaust openings, said raised regions being planar along surfaces generally parallel to said workpiece during levitation, said surfaces being above said work surface of said support structure.

3. The system of claim 1 wherein said work surface has an array of supply openings associated with each said exhaust opening.

4. The system of claim 2 wherein said pressure at said exhaust openings is maintained such that said exhaust openings have an exhaust capacity which exceeds a supply capacity of said continuous flow through said supply openings.

5. The system of claim 1 further comprising means for forming a partial vacuum at said exhaust openings.

6. The system of claim 1 further comprising inspection means for optically inspecting said workpiece that is adjacent to said work surface.

7. The system of claim 1 wherein said support structure includes a plurality of pressure chambers and a plurality of vacuum chambers, said pressure and vacuum chambers extending in parallel fashion along a lower side of a wall, said work surface being an upper side of said wall, each said pressure chamber being connected to a subset of said supply openings and to said source means, each said vacuum chamber being connected to a subset of said exhaust openings.

8. The system of claim 1 wherein said supply openings have a smaller cross sectional area than said exhaust openings and wherein said supply openings outnumber said exhaust openings.

9. The system of claim 1 further comprising pneumatic means for applying positive gas pressure to said workpiece in a direction opposite to said supply openings.

10. A method of manipulating workpieces comprising the steps of:
    positioning a workpiece adjacent to a work surface having a plurality of openings, including supply openings and exhaust openings interspersed Within an area of said workpiece;
    projecting gas through said supply openings at a positive pressure sufficient to position said workpiece in paced relationship from said work surface; and
    forming a negative pressure at said exhaust openings to evacuate said gas from between said workpiece and said work surface, including establishing an equilibrium condition in which said positive and negative pressures cooperate to maintain said workpiece in a position of substantially uniform spacing from said work surface.

11. The method of claim 10 further comprising a step of optically inspecting said workpiece.

12. The method of claim 10 wherein said step of positioning said workpiece includes locating a generally planar member adjacent to a work surface having a plurality of supply openings and having a plurality of exhaust openings, each exhaust opening being surrounded by a raised region of said work surface.

13. The method of claim 12 wherein said step of establishing said equilibrium condition includes utilizing said raised regions and exhaust openings as pinch valves.

14. The method of claim 10 wherein said step of positioning said workpiece includes locating a continuous web of flexible material adjacent to said work surface, said work surface being substantially planar with raised regions surrounding said exhaust openings.

15. The method of claim 10 further comprising a step of applying a flow of air on a side of said workpiece opposite to said work surface, thereby pressing said workpiece toward said work surface.

16. An inspection system comprising:
    a support structure for positioning an item of interest, said support structure having a generally planar work surface with at least four alternating arrays of supply openings and exhaust openings;

air pressure control means for establishing a positive pressure flow from each of said supply openings and establishing a negative pressure flow to each of said exhaust openings, thereby providing an equilibrium condition with respect to pneumatically supporting said item of interest in spaced relation from said work surface, said air pressure control means being connected to control levels of vacuum pressure at ends of said exhaust openings opposite to said item of interest; and inspection means for optically inspecting said item of interest when said item of interest is positioned by said support structure.

17. The inspection system of claim 16 wherein said support structure includes parallel positive pressure chambers and negative pressure chambers arranged in an alternating fashion, each said positive pressure chamber being in communication with an associated array of supply openings, each said negative pressure chamber being in communication with an associated array of exhaust openings, said air pressure control means and said supply and exhaust being cooperative to retard lateral flow from said supply openings to edges of said item of interest.

18. The inspection system of claim 17 wherein said support structure includes raised regions at said exhaust openings and includes depressed regions along said supply openings.

19. The inspection system of claim 17 wherein said supply openings are smaller than said exhaust openings and wherein said supply openings outnumber said exhaust openings.

20. The inspection system of claim 16 wherein exhaust openings are surrounded by raised regions having planar top surfaces.

\* \* \* \* \*